(12) United States Patent
Chua et al.

(10) Patent No.: US 9,422,543 B2
(45) Date of Patent: Aug. 23, 2016

(54) ISOLATION OF NUCLEIC ACID

(75) Inventors: Yii Leng Chua, Cambridge (GB); Allyson Victoria Ritchie, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 616 days.

(21) Appl. No.: 13/057,947

(22) PCT Filed: Aug. 7, 2009

(86) PCT No.: PCT/GB2009/001951
§ 371 (c)(1),
(2), (4) Date: Jul. 11, 2011

(87) PCT Pub. No.: WO2010/015835
PCT Pub. Date: Feb. 11, 2010

(65) Prior Publication Data
US 2011/0257386 A1   Oct. 20, 2011

(30) Foreign Application Priority Data

Aug. 8, 2008   (GB) .................................. 0814570.8

(51) Int. Cl.
C12N 15/10   (2006.01)

(52) U.S. Cl.
CPC ........ *C12N 15/1006* (2013.01); *C12N 15/1003* (2013.01)

(58) Field of Classification Search
None
See application file for complete search history.

(56) References Cited

U.S. PATENT DOCUMENTS

| | | | |
|---|---|---|---|
| 5,130,238 A | 7/1992 | Malek et al. | |
| 5,409,818 A | 4/1995 | Davey et al. | |
| 5,437,990 A | 8/1995 | Burg et al. | |
| 5,554,517 A | 9/1996 | Davey et al. | |
| 5,556,771 A | 9/1996 | Shen et al. | |
| 5,614,387 A | 3/1997 | Shen et al. | |
| 5,654,142 A | 8/1997 | Kievits et al. | |
| 5,834,254 A | 11/1998 | Shen et al. | |
| 5,849,544 A | 12/1998 | Harris et al. | |
| 5,888,779 A | 3/1999 | Kacian et al. | |
| 5,955,261 A | 9/1999 | Kohne | |
| 5,990,302 A | 11/1999 | Kuroita et al. | |
| 6,063,603 A | 5/2000 | Davey et al. | |
| 6,090,591 A | 7/2000 | Burg et al. | |
| 6,203,989 B1 | 3/2001 | Goldberg et al. | |
| 6,252,059 B1 | 6/2001 | McDonough et al. | |
| 6,355,792 B1 | 3/2002 | Michelsen et al. | |
| 6,410,276 B1 | 6/2002 | Burg et al. | |
| RE37,891 E | 10/2002 | Collins et al. | |
| 6,485,982 B1 | 11/2002 | Charlton | |
| 6,548,253 B1 | 4/2003 | Holschuh et al. | |
| 6,803,196 B1 | 10/2004 | Lyon et al. | |
| 6,806,047 B2 | 10/2004 | Goldberg et al. | |
| 7,718,421 B2 | 5/2010 | Chen et al. | |
| 2001/0018513 A1 | 8/2001 | Baker | |
| 2001/0041332 A1 | 11/2001 | Hillebrand et al. | |
| 2005/0282202 A1 | 12/2005 | Brolaski et al. | |
| 2006/0160085 A1* | 7/2006 | Hillebrand et al. | ............... 435/6 |
| 2008/0166703 A1* | 7/2008 | Himmelreich et al. | ........... 435/6 |

FOREIGN PATENT DOCUMENTS

| | | | |
|---|---|---|---|
| CN | 1781931 | 6/2006 | |
| EP | 0487628 | 6/1992 | |
| EP | 0512767 A1 | 11/1992 | |
| EP | 0629706 | 12/1994 | |
| EP | 0726310 | 8/1996 | |
| EP | 1234832 | 8/2002 | |
| JP | 2002531126 A | 9/2002 | |
| JP | 2007537134 A | 12/2007 | |
| JP | 5268963 B2 | 8/2013 | |
| WO | WO 99/23111 | 5/1999 | |
| WO | WO-99/29703 A2 | 6/1999 | |
| WO | WO-00/29562 A1 | 5/2000 | |
| WO | WO-00/34463 A1 | 6/2000 | |
| WO | WO 00/69872 A2 | 11/2000 | |
| WO | WO-02/48164 A2 | 6/2002 | |
| WO | WO 2004/055207 | 7/2004 | |
| WO | WO 2004055207 A1 * | 7/2004 | ............... C12Q 1/68 |
| WO | WO 2004/080597 | 9/2004 | |
| WO | WO-2005/011721 A2 | 2/2005 | |
| WO | WO-2005/045030 A1 | 5/2005 | |
| WO | WO 2008/035991 | 3/2008 | |

OTHER PUBLICATIONS

Nawrocki, J. (1991). Silica surface controversies, strong adsorption sites, their blockage and removal. Part II. Chromatographia, 31(3-4), 193-205.*
Michelsen et al., WO 2004055207, Jul. 2004, machine translation, Retreived on Nov. 14, 2013 from http://worldwide.espacenet.com.*
Sigma-Aldrich Buffer Learning Center, website capture of http://www.sigmaaldrich.com/life-science/core-bioreagents/biological-buffers/learning-center/buffer-reference-center.html on Jan. 8, 2009 from http://web.archive.org. Retrevied on Nov. 14, 2013.*
Hourfar et al., "High-Throughout Purification of Viral RNA Based on Novel Aqueous Chemistry for Nucleic Acid Isolation," *Clin. Chem.* 51: 1217-1222, 2005.
International Search Report (PCT/GB2009/001951) completed Nov. 9, 2009.
Written Opinion of the International Searching Authority (PCT/GB2009/001951) completed Nov. 9, 2009.
User Guide for Pico Pure TM DNA Extraction Kit, Version D, Catalog #KIT0103, Arcturus Systems for Microgenomics (2002) (15 pages).

(Continued)

*Primary Examiner* — Eric Olson
*Assistant Examiner* — Dale R Miller
(74) *Attorney, Agent, or Firm* — Clark & Elbing LLP

(57) ABSTRACT

A method for isolating a nucleic acid comprises: binding the nucleic acid to a solid phase at a first pH in the presence of a binding buffer, washing the bound nucleic acid with a wash solution, and eluting the nucleic acid from the solid phase at a second pH which is higher than the first pH. The wash solution comprises a buffer with a buffering range that encompasses a pH that is higher than the first pH, and the wash solution is at a pH that is within a buffering range of the binding buffer but lower than the buffering range of the buffer of the wash solution. Solutions, compositions, and kits for use in the methods are described.

47 Claims, 4 Drawing Sheets

(56) References Cited

OTHER PUBLICATIONS

User's Guide for AccuPrep Genomic DNA Extraction Kit, Cat. No. K-3032, Bioneer Corporation, (2004) (10 pages).
Information sheet for mirVana™ miRNA Isolation, Cat. No. 1560, Protocol, Ambion, Inc., received Jan. 19, 2016 (10 pages).
*RNeasy® Mini Handbook.* Qiagen, 1-11 (2001).
*QIAquick® Spin Handbook.* Qiagen, 1-18 (2002).
Instruction manual for RiboPure™-WBC, Cat. No. 1903, Ambion, Inc., received Jan. 19, 2016 (28 pages).
"Bioworld TRIS Buffer, 1.0 M solution, pH 6.5, Sterile filtered," <www.bio-world.com/productinfo/4_847_925/131269/TRIS-Buffer-M-solution-pH-Sterile-filtered.html>, received Jan. 19, 2016 (1 page).
Instruction manual for PowerSoil™ DNA Isolation Kit, Cat. Nos. 12888-50 and 12888-100, Mo Bio Labratories, Inc., received Jan. 19, 2016 (8 pages).
Instruction manual for UltraClean™ Fecal DNA Kit, Cat. No. 12811-100, Mo Bio Labratories, Inc., received Jan. 19, 2016 (5 pages).
Instruction manual for UltraClean™ Plant DNA Isolation Kit, Cat. No. 13000-50, Mo Bio Labratories, Inc., received Jan. 19, 2016 (7 pages).
Boom et al., "Rapid and simple method for purification of nucleic acids," J Clin Microbiol. 28(3):495-503 (1990).
Cacace et al., "The Hofmeister series: salt and solvent effects on interfacial phenomena," Q Rev Biophys. 30(3):241-77 (1997) (Abstract only).

* cited by examiner

ISOLATION OF NUCLEIC ACID

CROSS-REFERENCE TO RELATED APPLICATIONS

This application is the U.S. National Stage filing under 35 U.S.C. §371 of International Application PCT/GB2009/001951, filed Aug. 7, 2009, which claims benefit of Great Britain Application No. 0814570.8, filed Aug. 8, 2008.

This invention relates to improved methods for isolation of nucleic acid, and to solutions, compositions, and kits for use in the methods.

Conventional methods for isolation of nucleic acid use chaotropic agents, such as guanidinium thiocyanate, and organic solvents to lyse cells, and denature proteins (including nucleases, which would otherwise degrade the nucleic acid). For example, Boom et al. (Journal of Clinical Microbiology, 1990, Vol. 28(3): 495-503) describes a method in which a sample containing human serum or urine is contacted with silica particles in the presence of a lysis/binding buffer containing guanidinium thiocyanate. Released nucleic acid binds to the silica particles, which are then washed with a wash buffer containing guanidinium thiocyanate, then with ethanol, and then acetone. The bound nucleic acid is subsequently eluted in an aqueous low salt buffer (Tris-HCl, EDTA, pH 8.0).

A disadvantage of such methods, however, is that chaotropic agents and organic solvents are highly inhibitory to enzymatic reactions. Residual amounts of these substances carried over into the eluted sample can interfere with subsequent enzymatic processing of the isolated nucleic acid, for example in nucleic acid sequencing or amplification. Use of chaotropic agents and organic solvents is also undesirable because these reagents are toxic and difficult to handle, and require special provision for their disposal. A further disadvantage of use of chaotropic agents is that they are required in high molarities and tend to precipitate out of solution during storage, especially refrigerated storage. Solutions containing these agents may require heating to re-dissolve the chaotropic agent before use.

The requirement for chaotropic salts and organic solvents is avoided in a method described by Hourfar et al. (Clinical Chemistry, 2005, 51(7): 1217-1222). Plasma sample is mixed with magnetic silica particles in the presence of a lysis/binding buffer containing a kosmotropic salt (ammonium sulphate) before addition of proteinase K. Following separation, the magnetic particles are washed with wash buffer containing proteinase K, and eluted in elution buffer (Tris-HCl, pH 8.5) at 80° C. Whilst nucleic acid can be obtained in reasonable yields using such methods, it is desired to obtain even greater yield of nucleic acid. It is also desired to provide methods that can be carried out without any requirement for enzymes, such as proteinase K. Use of enzymes increases the cost of carrying out the methods, and it is necessary to store the enzymes separately under special conditions (for example, at reduced temperature, or in lyophilised form) to maintain their stability.

According to the invention there is provided a method for isolating a nucleic acid, which comprises:
  (i) binding the nucleic acid to a solid phase at a first pH in the presence of a binding buffer;
  (ii) washing the bound nucleic acid with a wash solution; and
  (iii) eluting the nucleic acid from the solid phase at a second pH which is higher than the first pH;
wherein the wash solution comprises a buffer with a buffering range that encompasses a pH that is higher than the first pH, and the wash solution is at a pH that is within a buffering range of the binding buffer but lower than the buffering range of the buffer of the wash solution (i.e. the wash buffer).

We have found that methods of the invention provide surprising increases in the yield of nucleic acid obtained compared with prior art methods, for example the method described by Hourfar et al. It is believed that the improved yield obtained using methods of the invention is due to reduced amounts of nucleic acid being removed from the solid phase during the washing step, and/or increased amounts of nucleic acid being released from the solid phase during the elution step, compared with prior art methods.

Improved yields of nucleic acid may be obtained using methods of the invention without any requirement for enzyme (such as protease) to be present in the wash solution, or for use of organic solvents or chaotropic agents. The wash solution is thereby simplified compared, for example, with the wash solution required for the method of Hourfar et al, and there is no requirement for separate storage of protease or other enzyme. Because there is no requirement for chaotropic agents or organic solvents, inhibition of subsequent enzymatic processing of the isolated nucleic acid by such agents or solvents can be avoided.

Preferably the first pH is an acidic pH, preferably in the range pH 3-6, or pH 3-5. Preferably the second pH is at least pH 6.5, preferably at least pH 7.0, or an alkaline pH. Suitably the second pH is in the range pH 6.5-10, preferably pH 7-9. Such pH values are typical of those used with solid phases such as silica-based solid phases that are able to bind nucleic acid at a lower pH and release nucleic acid at a higher pH. Extremes of pH are avoided which might otherwise damage the nucleic acid.

Preferably the buffering range of the wash buffer is higher than the first pH (i.e. a lower end of the buffering range of the wash buffer is greater than the first pH). Preferably the buffering range of the wash buffer is higher than pH 5.0. Preferably the second pH is within the buffering range of the wash buffer. This is preferred because it is believed that the pH of residual wash solution present on the solid phase after the washing step may then be converted most efficiently to the second pH during the elution step thereby maximising the amount of nucleic acid that is released from the solid phase.

Preferably the pH of the wash solution is pH 6.3 or less, preferably pH 6.0 or less, more preferably from pH 3.0 to pH 6.0. Use of wash solution at a pH within these preferred ranges is compatible with buffer ranges of preferred binding and wash buffers.

Preferably the first pH is within the buffering range of the binding buffer so that the pH of the binding step is controlled by the binding buffer. Preferably a lower end of the buffering range of the binding buffer is at pH 3.0 or higher so that extremes of pH are avoided in the binding step.

The buffering ranges of buffers commonly used in lysis, binding, washing, and elution buffers are known to those of skill in the art. The pKa value and buffering range of some important biological buffers, sorted by buffering range, is given in Table 1 below (taken from Sigma-Aldrich).

TABLE 1

| Effective pH range | pKa 25° C. | Buffer |
|---|---|---|
| 1.2-2.6 | 1.97 | maleate (pK1) |
| 1.7-2.9 | 2.15 | phosphate (pK1) |
| 10.0-11.4 | 10.70 | CABS |
| 10.5-12.0 | 11.12 | piperidine |

TABLE 1-continued

| Effective pH range | pKa 25° C. | Buffer |
|---|---|---|
| 2.2-3.6 | 2.35 | glycine (pK1) |
| 2.2-6.5 | 3.13 | citrate (pK1) |
| 2.5-3.8 | 3.14 | glycylglycine (pK1) |
| 2.7-4.2 | 3.40 | malate (pK1) |
| 3.0-4.5 | 3.75 | formate |
| 3.0-6.2 | 4.76 | citrate (pK2) |
| 3.2-5.2 | 4.21 | succinate (pK1) |
| 3.6-5.6 | 4.76 | acetate |
| 3.8-5.6 | 4.87 | propionate |
| 4.0-6.0 | 5.13 | malate (pK2) |
| 4.9-5.9 | 5.23 | pyridine |
| 5.0-6.0 | 5.33 | piperazine (pK1) |
| 5.0-7.4 | 6.27 | cacodylate |
| 5.5-6.5 | 5.64 | succinate (pK2) |
| 5.5-6.7 | 6.10 | MES |
| 5.5-7.2 | 6.40 | citrate (pK3) |
| 5.5-7.2 | 6.24 | maleate (pK2) |
| 5.5-7.4 | 1.70, 6.04, 9.09 | histidine |
| 5.8-7.2 | 6.46 | bis-tris |
| 5.8-8.0 | 7.20 | phosphate (pK2) |
| 6.0-12.0 | 9.50 | ethanolamine |
| 6.0-7.2 | 6.59 | ADA |
| 6.0-8.0 | 6.35 | carbonate (pK1) |
| 6.1-7.5 | 6.78 | ACES |
| 6.1-7.5 | 6.76 | PIPES |
| 6.2-7.6 | 6.87 | MOPSO |
| 6.2-7.8 | 6.95 | imidazole |
| 6.3-9.5 | 6.80, 9.00 | BIS-TRIS propane |
| 6.4-7.8 | 7.09 | BES |
| 6.5-7.9 | 7.14 | MOPS |
| 6.8-8.2 | 7.48 | HEPES |
| 6.8-8.2 | 7.40 | TES |
| 6.9-8.3 | 7.60 | MOBS |
| 7.0-8.2 | 7.52 | DIPSO |
| 7.0-8.2 | 7.61 | TAPSO |
| 7.0-8.3 | 7.76 | triethanolamine (TEA) |
| 7.0-9.0 | 0.91, 2.10, 6.70, 9.32 | pyrophosphate |
| 7.1-8.5 | 7.85 | HEPPSO |
| 7.1-9.0 | | Tris-HCl |
| 7.2-8.5 | 7.78 | POPSO |
| 7.4-8.8 | 8.05 | tricine |
| 7.5-10.0 | 8.10 | hydrazine |
| 7.5-8.9 | 8.25 | glycylglycine (pK2) |
| 7.5-9.0 | 8.06 | Trizma (tris) |
| 7.6-8.6 | 8.00 | EPPS, HEPPS |
| 7.6-9.0 | 8.26 | BICINE |
| 7.6-9.0 | 8.30 | HEPBS |
| 7.7-9.1 | 8.40 | TAPS |
| 7.8-9.7 | 8.80 | 2-amino-2-methyl-1,3-propanediol (AMPD) |
| 8.2-9.6 | 8.90 | TABS |
| 8.3-9.7 | 9.00 | AMPSO |
| 8.4-9.6 | 9.06 | taurine (AES) |
| 8.5-10.2 | 9.23, 12.74, 13.80 | borate |
| 8.6-10.0 | 9.50 | CHES |
| 8.7-10.4 | 9.69 | 2-amino-2-methyl-1-propanol (AMP) |
| 8.8-10.6 | 9.78 | glycine (pK2) |
| 8.8-9.9 | 9.25 | ammonium hydroxide |
| 8.9-10.3 | 9.60 | CAPSO |
| 9.5-11.1 | 10.33 | carbonate (pK2) |
| 9.5-11.5 | 10.66 | methylamine |
| 9.5-9.8 | 9.73 | piperazine (pK2) |
| 9.7-11.1 | 10.40 | CAPS |
| | 12.33 | phosphate (pK3) |

Methods of the invention may be carried out using conventional binding buffers and/or elution buffers for use with a solid phase that is able to bind the nucleic acid in the presence of binding buffer at the first pH, and from which the nucleic acid can be eluted at the second pH.

The solid phase preferably comprises an ionisable group, which changes charge according to the ambient conditions. The pKa of the ionisable group is appropriate to the conditions at which it is desired to bind nucleic acid to and release nucleic acid from the solid phase. Generally, nucleic acid will bind to the solid phase at a pH below or roughly equal to the pKa, and will be released at a higher pH (usually above the pKa). Suitable solid phases for binding a nucleic acid at a first pH, and elution of bound nucleic acid at a second pH that is higher than the first pH, are well known to those of ordinary skill in the art. For example, at the first pH the solid phase may comprise a positive charge, and at the second pH the solid phase may have a less positive, neutral, or negative charge. Alternatively or additionally, at the first pH the solid phase may comprise a neutral or less negative charge, and at the second pH the solid phase may have a negative or more negative charge. Such changes in charge allow the nucleic acid to be adsorbed to the solid phase at the first pH, and released at the second pH.

For example, the solid phase may comprise a negatively ionisable group with a pKa between the first and second pH. Nucleic acid will bind to the solid phase when the solid phase is neutral or less negatively charged, and will be released when the solid phase is negatively or more negatively charged.

Alternatively, or additionally, the solid phase may comprise a positively ionisable group with a pKa between the first and second pH. Nucleic acid will bind to the solid phase when the solid phase is positively charged, and will be released when the solid phase is neutral or less positively charged.

Examples of solid phases that may be used in accordance with the invention include solid phases that comprise inorganic oxides, such as silica or glass (for example, as described in Boom et al, or Hourfar et al), or aluminium oxide, sugar polymers, or charge-switch materials (for example, as described in WO 02/48164).

The solid phase may be in any suitable form, for example comprising a membrane, gel, or particles, for example magnetic particles. Silica membrane or gel, and magnetic silica particles are preferred examples. Silica membrane is particularly preferred. This is less expensive than magnetic silica particles (used for example by Hourfar, et al.) and does not require refrigerated storage, unlike magnetic silica particles.

Whilst binding of nucleic acid to the solid phase may be enhanced by the presence of a chaotropic agent, residual amounts of such agents inhibit enzymatic processing of the isolated nucleic acid and are toxic, so it is preferred that methods of the invention are carried out in the absence of a chaotropic agent.

Preferably the solid phase is a solid phase to which binding of nucleic acid is enhanced by the presence of a kosmotropic agent. Preferably binding of the nucleic acid to the solid phase is carried out in the presence of a kosmotropic agent. Such agents are known to enhance binding of nucleic acid to solid phases such as silica-based solid phases.

The terms "chaotropic" and "kosmotropic" agent originate from the Hofmeister series (Cacace et al., Q Rev Biophys 1997; 30:241-77), which divides these agents depending on their influence on the structure of macromolecules and water. A chaotrope may be defined as a substance that breaks solvent structure, and a kosmotrope as a substance that enhances solvent structure. FIG. 1 of Cacace et al shows the Hofmeister series and commonly occurring organic solutes with effects on protein structure/function. Examples of chaotropic agents are known to those in the art, and include sodium iodide, sodium perchlorate, guanidinium thiocyanate and guanidinium hydrochloride. Examples of kosmotropic agents are known to those in the art, and include ammonium sulphate and lithium chloride.

According to the invention there is also provided a method for isolating a nucleic acid from a cell, which comprises lysing the cell to release the nucleic acid from the cell, and isolating the released nucleic acid using a method of the invention.

Lysis is preferably carried out using the binding buffer. Binding buffers that may be used for cell lysis are known to those of ordinary skill in the art. The lysis buffer used by Boom et al. comprises guanidinium thiocyanate, Tris hydrochloride, pH 6.4, EDTA (adjusted to pH 8), and Triton X-100. However, it is preferred that the lysis buffer does not include a chaotropic agent. Preferred lysis/binding buffers for use according to the invention comprise a kosmotropic agent. Preferably the buffer is an acidic buffer, suitably a strong acidic buffer with a pKa (25° C.) in the range 3-5.

Further improved yield of nucleic acid may be obtained by elution of the nucleic acid from the solid phase at a temperature above ambient temperature, for example 50-90° C., 60-85° C., or 70-80° C.

Preferably the nucleic acid is eluted from the solid phase in the presence of an elution buffer. Preferably the second pH is within a buffering range of the elution buffer so that the pH of elution is controlled by the elution buffer.

In a preferred embodiment, the buffering range of the elution buffer overlaps with, encompasses, or is encompassed by the buffering range of the wash buffer. This helps to ensure that the pH of residual wash solution on the solid phase after the washing step is readily increased towards the second pH during elution.

There is further provided according to the invention a solution for use as a wash solution in a method of the invention.

According to the invention there is also provided a solution comprising a buffer for washing a solid phase to which a nucleic acid is bound at a first pH and eluted at a second, higher pH, wherein the pH of the solution is pH 6.3 or less, preferably pH 6.0 or less, more preferably from pH 3.0 to pH 6.0, and is lower than a buffering range of the buffer.

Preferably the solution of the invention does not include a chaotropic agent. Preferably the solution does not include an organic solvent.

Preferably the or each buffering range of the buffer is higher than pH 5.0, preferably higher than pH 6.0, Preferably the buffering range of the buffer overlaps with, is encompassed by, or encompasses the range pH 6.5-10. In some preferred embodiments the buffering range of the buffer is higher than pH 7.0.

Preferably the pH of a solution of the invention is pH 5.0 or less, preferably from pH 3.5 to 5.

Examples of preferred buffers for the wash solution or solution of the invention include a Tris buffer, preferably Tris-HCl, and a 2-(N-morpholino)ethanesulfonic acid (MES) buffer. The buffering range for Tris-HCl buffer is pH 7.1 to 9. The buffering range for MES buffer is pH 5.5-6.7.

There is further provided according to the invention a composition in dry form that when dissolved in a liquid provides a solution according to the invention. The composition may be a lyophilisate. Such compositions can be prepared, for example, by providing a solution of the invention and lyophilising the solution to form the composition in dry form.

In a preferred embodiment, the wash solution or solution of the invention further comprises a detergent. Detergent may assist in removing inhibitors that may interfere with subsequent processing of the isolated nucleic acid. Suitable examples are ionic detergents such as lithium dodecyl sulphate (LDS), or non-ionic detergents such as NP-40 and Triton-X.

It will be appreciated that detergent will not be present in a dry composition of the invention. If it is desired to include a detergent in a solution prepared using a composition in dry form, this may be added after the composition has been dissolved in aqueous solution.

Improved yield of nucleic acid may be obtained using methods of the invention even without inclusion of a protease in the wash solution. Preferably the wash solution or solution of the invention does not include a protease.

According to the invention, there is also provided a kit for isolation of a nucleic acid, which comprises:
  i) a binding buffer for binding the nucleic acid to a solid phase at a first pH;
  ii) a wash solution that comprises a buffer with a buffering range that encompasses a pH that is higher than the first pH, wherein the wash solution is at a pH that is within a buffering range of the binding buffer but lower than the buffering range of the buffer of the wash solution; and optionally
  iii) a solution for eluting the nucleic acid from the solid phase, wherein the solution is at a second pH that is higher than the first pH.

According to the invention, there is also provided a kit for isolation of a nucleic acid, which comprises:
  i) a binding buffer for binding the nucleic acid to a solid phase at a first pH;
  ii) a composition in dry form that when dissolved in a liquid provides a wash solution that comprises a buffer with a buffering range that encompasses a pH that is higher than the first pH, wherein the wash solution is at a pH that is within a buffering range of the binding buffer but lower than the buffering range of the buffer of the wash solution; and optionally
  iii) a composition in dry form that when dissolved in a liquid provides a solution for eluting the nucleic acid from the solid phase, wherein the solution is at a second pH that is higher than the first pH.

Such kits may be used to carry out a method of the invention.

The binding buffer may be provided as a solution or in dry form (for example as a lyophilisate) for dissolving in a liquid.

The composition in dry form that when dissolved in a liquid provides a wash solution, and/or the composition in dry form that when dissolved in a liquid provides an elution solution, may be a lyophilisate. The lyophilisate may be prepared, for example, by providing the wash solution or the elution solution and lyophilising the solution to form the composition in dry form.

The liquid for dissolving the binding buffer, or a composition of the invention is suitably water, or an aqueous solution.

The wash solution of a kit of the invention is preferably a solution of the invention.

The composition in dry form for providing the wash solution is preferably a composition of the invention.

Preferably the kit does not comprise a chaotropic agent, nor an organic solvent. Preferably the binding buffer of the kit comprises a kosmotropic agent. Examples of suitable kosmotropic agents include ammonium sulphate and lithium chloride. Ammonium sulphate is preferred.

A kit of the invention may further comprise a solid phase to which the nucleic acid is able to bind. Suitable solid phases are discussed above. A preferred solid phase comprises a negatively ionisable group with a pKa between a first pH at which the nucleic acid is able to bind to the solid phase, and a second pH at which the nucleic acid can be eluted from the solid phase. Preferably the solid phase comprises an inorganic oxide, preferably silica.

A kit of the invention may further comprise a protease for use with the binding buffer. Preferably the protease is in lyophilised form, separate from the binding buffer (and separate from the other components of the kit).

A kit of the invention may include instructions for carrying out nucleic acid isolation using the components of the kit.

A kit of the invention may further comprise reagents required for amplification and/or detection of nucleic acid once isolated.

A kit of the invention will typically be provided with the components of the kit (i.e. the binding buffer, the wash solution (or the composition in dry form that when dissolved in a liquid provides the wash solution), and (if present) the elution solution (or the composition in dry form that when dissolved in a liquid provides the elution solution) separately packaged, or stored in separate compartments of a container in which the kit is provided.

The Applicant has appreciated that during the washing step, the wash buffer should remain close to the first pH when mixed with residual binding buffer retained on the solid phase, so that nucleic acid remains bound to the solid phase and is not washed away. However, during the elution step, residual wash buffer should change towards the second pH when mixed with elution solution for effective release of nucleic acid from the solid phase. Without being bound by theory, it is believed that the improved yield obtainable using methods of the invention arises because: (i) the wash solution does not remove significant amounts of nucleic acid from the solid phase during the washing step (because the pH of the washing solution is within the buffering range of the binding buffer); and (ii) the pH of residual wash buffer retained on the solid phase readily changes towards the second pH when mixed with elution solution (due to the buffering range of the wash buffer).

There is also provided according to the invention use of a solution or composition of the invention, or use of a kit of the invention for isolation of a nucleic acid.

We have found that methods of the invention are capable of extracting as few as 25 copies of nucleic acid, in particular viral RNA, from a biological sample. At low concentrations of virus the yield of nucleic acid obtained using methods of the invention is as good as, if not more reproducible, than that of a typical nucleic acid extraction method, which uses chaotropic salts and organic solvents.

Methods of the invention can be performed with buffer formulations that are non-hazardous and do not require special disposal, unlike some conventional nucleic acid extraction methods that use chaotropic salts and/or organic solvents. The buffer formulations used are stable and do not require refrigeration or heating before use to re-dissolve components that have precipitated during storage. The methods may be used in nucleic acid isolation and testing in hospitals and laboratories, and are especially important for on-site nucleic acid testing in the field and for point-of-care nucleic acid testing.

Embodiments of the invention are now described, by way of example only, with reference to the accompanying drawings in which.

EXAMPLE 1

Comparison of Yield of Nucleic Acid Obtained Using Acidic and Alkaline Wash Buffers at pH 4 and pH5

HIV viral RNA was isolated using an aqueous-based lysis buffer (comprising Tris Acetate, pH 4.0), bound to a silica-based solid phase and washed with wash buffers comprising 10 mM Tris-HCl (buffering range, pH 7.1 to 9), at pH 4 or 5, 10 mM sodium citrate (buffering range, pH 3.0 to 6.2), at pH 4 or 5, or 10 mM Tris Acetate (buffering range, pH 3.6-5.6), at pH 4 or 5. The 10 mM Tris-HCl solutions at pH 4 and 5 are embodiments of a solution of the invention.

Figure 1:
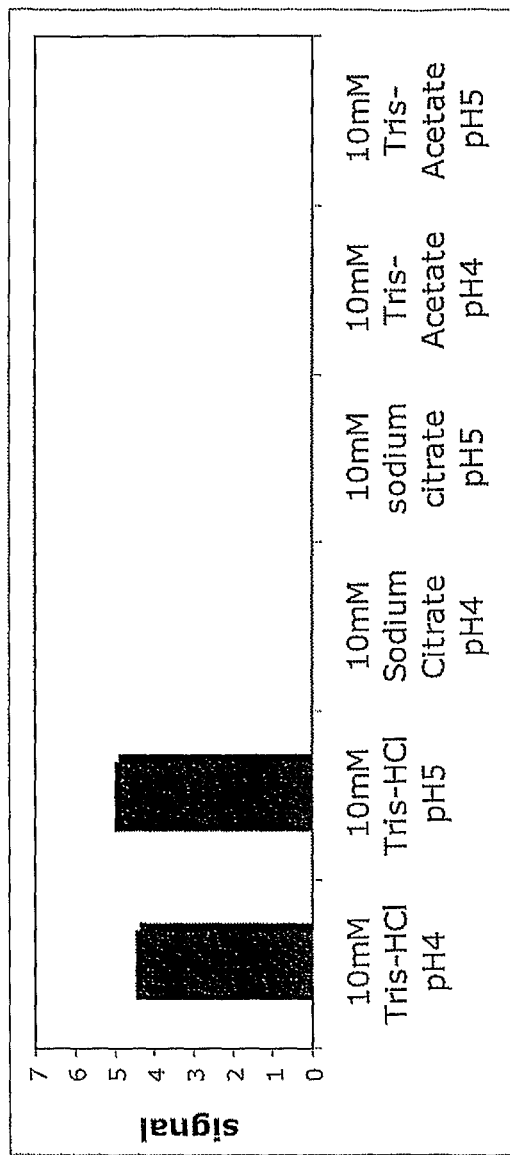
FIG. 1 shows a comparison of yield of nucleic acid obtained using acidic and alkaline wash buffers at pH 4 and pH 5.

Washed nucleic acid bound to the solid phase was eluted with elution buffer (comprising Tris-HCl, pH 8.5). The isolated nucleic acid was amplified and detected. FIG. 1 shows the average detection signal strength, error bars indicate the standard error of the mean.

FIG. 1 shows that the yield of nucleic acids obtained with 10 mM Tris-HCl, pH 4 and pH 5 was significantly higher than with 10 mM sodium citrate, pH 4 and 5, and with 10 mM Tris Acetate, pH 4 and 5.

It is believed that the acidic wash buffers were not as effective as 10 mM Tris-HCl, pH 4 or 5, because residual buffer left on the solid phase lowers the pH of the elution buffer, making elution of nucleic acid less efficient and so reducing yield.

EXAMPLE 2

Figure 2:
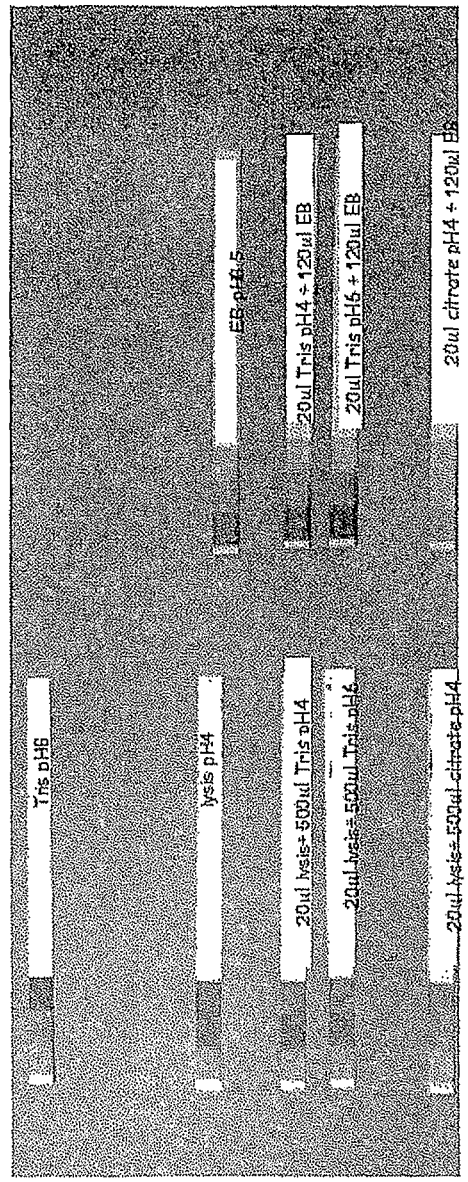
FIG. 2 shows the effect of residual lysis buffer on wash buffer pH, and the effect of residual wash buffer on elution buffer pH.

Effect of Residual Lysis Buffer on Wash Buffer pH, and Effect of Residual Wash Buffer on Elution Buffer PH The interactions between residual lysis buffer and wash buffer, and between residual wash buffer and elution buffer, were investigated by mixing these buffers. 20 µl of lysis buffer (comprising Tris Acetate, pH 4), was mixed with 500 µl of wash buffer (10 mM Tris-HCl, pH 4, 10 mM Tris-HCl, pH 6, or 10 mM sodium citrate, pH 4), and 20 µl of wash buffer (10 mM Tris-HCl, pH 4, 10 mM Tris-HCl, pH 6, or 10 mM sodium citrate, pH 4) was mixed with 120 µl of elution buffer (comprising Tris-HCl, pH 8.5), to illustrate the interactions of the various buffers. The pH of the mixtures was measured with pH paper. The results are shown in FIG. 2.

The results show that 10 mM Tris-HCl, pH 4, and 10 mM Tris-HCl, pH 6, remains acidic when mixed with lysis buffer. When Tris-HCl, pH 4, or Tris-HCl, pH 6, was mixed with elution buffer, the mixture remained at pH 8.5. However, when 10 mM sodium citrate was mixed with elution buffer, the resulting solution has an acidic pH.

EXAMPLE 3

Comparison of Yield of Nucleic Acid Obtained at Different Wash Buffer pH (Using Wash Buffer Comprising MES)

Figure 3:
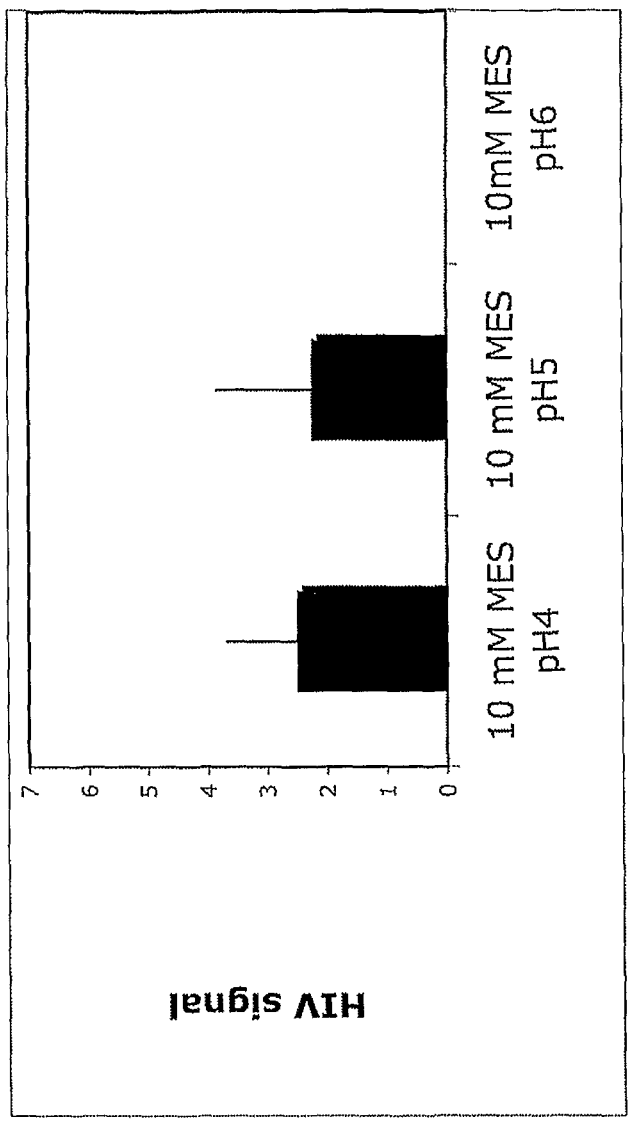
FIG. 3 shows a comparison of yield of nucleic acid obtained at different wash buffer pH (using wash buffer comprising MES)

HIV viral RNA was isolated using an aqueous-based lysis buffer (comprising Tris Acetate, pH 4.0), bound to a silica-based solid phase and washed with 10 mM MES (buffering range, pH 5.5 to 6.7), pH 4, 5 or 6. Nucleic acid was eluted with elution buffer (10 mM Tris-HCl, pH 8.5). The isolated nucleic acid was amplified and detected. FIG. 3 shows the average detection signal strength, error bars indicate the standard error of the mean.

The results show that the yield of nucleic acid obtained at pH 4 and 5 (lower than the buffering range of MES buffer) is significantly higher than at pH 6 (within the buffering range of MES buffer).

It is concluded that improved yield is obtained by use of a wash buffer at an acidic pH that is lower than the buffering range of the wash buffer.

EXAMPLE 4

Comparison of RNA Recovery Obtained Using a Method of the Invention Compared with a Qiagen Method of Nucleic Acid Isolation Viral RNA was isolated from HIV positive plasma samples using a method of the invention, and a Qiagen method of nucleic acid isolation. The isolated nucleic acid was then amplified and detected.

The method according to an embodiment of the invention was as follows:

Lysis buffer (comprising sodium citrate, pH 4.5) was mixed with a plasma sample and incubated before adding proteinase K. The mixture was incubated, then loaded onto a silica or glass fibre solid phase. Bound nucleic acid was washed with wash buffer (Tris-HCl, pH 3.8), and eluted with elution buffer (comprising Tris-HCl, 8.5) at 75-80° C.

Figure 4:
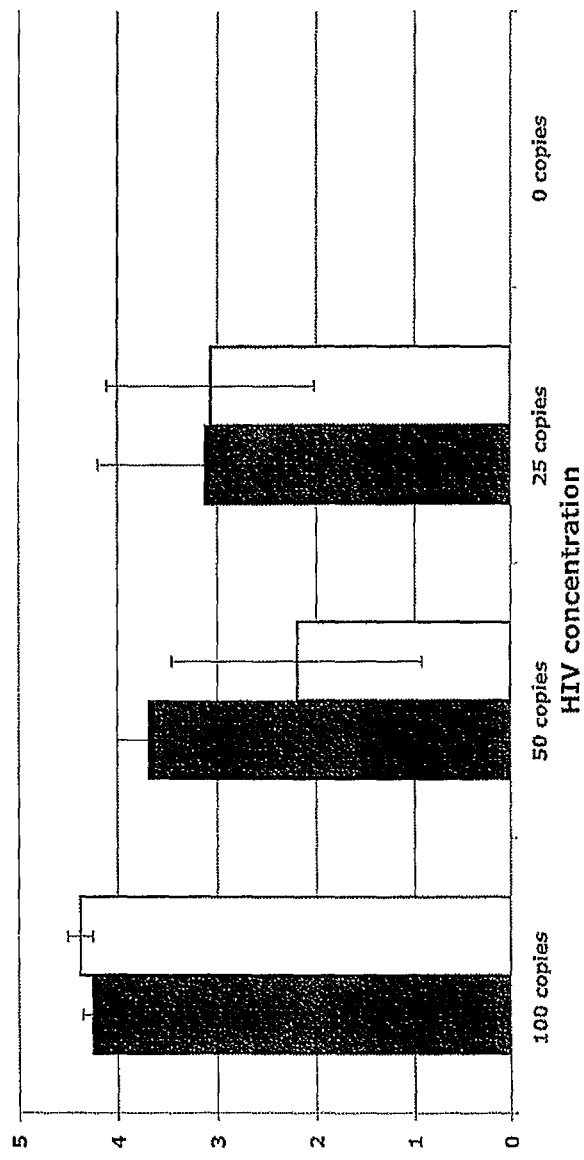
FIG. 4 shows the results of RNA recovery obtained using a method of the invention compared with a Qiagen method of nucleic acid isolation.

FIG. 4 shows the average signal strength, error bars show the standard error of the mean. The results for the method according to an embodiment of the invention are shown by the black columns, and the results for the Qiagen method are shown by the white columns.

The results shown in FIG. 4 demonstrate that methods of the invention are capable of extracting as few as 25 copies of nucleic acid, in particular viral RNA, from a biological sample. At low concentrations of virus the yield of nucleic acid obtained using the method according to an embodiment of the invention is as good as, if not more reproducible, than that of a typical nucleic acid extraction method, which uses chaotropic salts and organic solvents.

The buffer formulations used are non-hazardous and do not require special disposal, unlike some conventional nucleic acid extraction methods that use chaotropic salts and/or organic solvents. The buffer formulations used are stable and do not require refrigeration. The methods may be used in nucleic acid isolation and testing in hospitals and laboratories, and are especially important for on-site nucleic acid testing in the field and for point-of-care nucleic acid testing.

The invention claimed is:

1. A method for isolating a nucleic acid, which comprises:
   (i) binding the nucleic acid to a solid phase at a first pH in the presence of a binding buffer, wherein the first pH is an acidic pH;
   (ii) washing the bound nucleic acid with a wash solution; and
   (iii) eluting the nucleic acid from the solid phase at a second pH which is higher than the first pH;
wherein the wash solution comprises a buffer with a buffering range that encompasses a pH that is higher than the first pH, and the wash solution is at a pH that is within a buffering range of the binding buffer but lower than the buffering range of the buffer of the wash solution, wherein the pH of the wash solution is pH 6.0 or less, and wherein the method is carried out in the absence of an organic solvent.

2. The method of claim 1, wherein the buffering range of the wash buffer is higher than the first pH.

3. The method of claim 1, wherein the second pH is within the buffering range of the wash buffer.

4. The method of claim 1, wherein the buffering range of the wash buffer is higher than pH 5.0.

5. The method of claim 1, wherein the first pH is in the range pH 3-6.

6. The method of claim 1, wherein the second pH is in the range pH 6.5-10.

7. The method of claim 1, wherein the first pH is within the buffering range of the binding buffer.

8. The method of claim 1, wherein a lower end of the buffering range of the binding buffer is at pH 3.0 or higher.

9. The method of claim 1, wherein the method is carried out in the absence of a chaotropic agent.

10. The method of claim 1, wherein binding of the nucleic acid to the solid phase is carried out in the presence of a kosmotropic agent.

11. The method of claim 10, wherein the kosmotropic agent is ammonium sulphate.

12. The method of claim 1, wherein the solid phase comprises a negatively ionisable group with a pKa between the first and second pH.

13. The method of claim 1, wherein the solid phase comprises an inorganic oxide.

14. The method of claim 1 further comprising, prior to steps i)-iii), isolating said nucleic acid from a cell by lysing the cell to release the nucleic acid.

15. The method of claim 14, wherein lysis is carried out using the binding buffer.

16. The method of claim 1, wherein the binding buffer comprises a kosmotropic agent.

17. The method of claim 1, wherein the nucleic acid is eluted from the solid phase at a temperature above ambient temperature.

18. The method of claim 1, wherein the nucleic acid is eluted from the solid phase in the presence of an elution buffer, wherein the second pH is within a buffering range of the elution buffer.

19. The method of claim 18, wherein the buffering range of the elution buffer overlaps with or is encompassed by the buffering range of the wash buffer.

20. The method of claim 5, wherein the first pH is in the range pH 3-5.

21. The method of claim 6, wherein the second pH is in the range pH 7-9.

22. The method of claim 1, wherein the pH of the wash solution is from pH 3.0 to pH 6.0.

23. The method of claim 13, wherein the inorganic oxide is silica.

24. A kit for isolation of a nucleic acid comprising:
   i) a binding buffer for binding the nucleic acid to a solid phase at a first pH;
   ii) a wash solution that comprises a buffer with a buffering range that encompasses a pH that is higher than the first pH, wherein the wash solution is at a pH that is within a buffering range of the binding buffer but lower than the buffering range of the wash buffer; and optionally
   iii) a solution for eluting the nucleic acid from the solid phase, wherein the solution is at a second pH that is higher than the first pH.

25. The kit of claim 24, wherein the pH of the wash solution is pH 6.0 or less.

26. The kit of claim 25, wherein the pH of the wash solution is from pH 3.0 to pH 6.0.

27. The kit of claim 24, wherein the or each buffering range of the buffer is higher than pH 6.0.

28. The kit of claim 24, wherein the kit does not comprise a chaotropic agent and an organic solvent.

29. The kit of claim 24, wherein the binding buffer comprises a kosmotropic agent.

30. The kit of claim 24 further comprising a solid phase to which the nucleic acid is able to bind in the presence of the binding buffer at the first pH, and from which the nucleic acid can be eluted at the second pH.

31. The kit of claim 30, wherein the solid phase comprises a negatively ionisable group with a pKa between a first pH at which the nucleic acid is able to bind to the solid phase, and a second pH at which the nucleic acid can be eluted from the solid phase.

32. The kit of claim 30, wherein the solid phase comprises an inorganic oxide.

33. The kit of claim 32, wherein the inorganic oxide is silica.

34. The kit of claim 24 further comprising a protease separate from the binding buffer.

35. The kit of claim 34, wherein the protease is in lyophilised form.

36. A kit for isolation of a nucleic acid comprising:
   i) a binding buffer for binding the nucleic acid to a solid phase at a first pH;
   ii) a composition in dry form that when dissolved in a liquid provides a wash solution that comprises a buffer with a buffering range that encompasses a pH that is higher than the first pH, wherein the wash solution is at a pH that is within a buffering range of the binding buffer but lower than the buffering range of the buffer of the wash solution; and optionally
   iii) a composition in dry form that when dissolved in a liquid provides a solution for eluting the nucleic acid from the solid phase, wherein the solution is at a second pH that is higher than the first pH.

37. The kit of claim 36, wherein the pH of the wash solution is pH 6.0 or less.

38. The kit of claim 37, wherein the pH of the wash solution is from pH 3.0 to pH 6.0.

39. The kit of claim 36, wherein the or each buffering range of the buffer is higher than pH 6.0.

40. The kit of claim 36, wherein the kit does not comprise a chaotropic agent and an organic solvent.

41. The kit of claim 36, wherein the binding buffer comprises a kosmotropic agent.

42. The kit of claim 36 further comprising a solid phase to which the nucleic acid is able to bind in the presence of the binding buffer at the first pH, and from which the nucleic acid can be eluted at the second pH.

43. The kit of claim 42, wherein the solid phase comprises a negatively ionisable group with a pKa between a first pH at which the nucleic acid is able to bind to the solid phase, and a second pH at which the nucleic acid can be eluted from the solid phase.

44. The kit of claim 42, wherein the solid phase comprises an inorganic oxide.

45. The kit of claim 44, wherein the inorganic oxide is silica.

46. The kit of claim 36, further comprising a protease separate from the binding buffer.

47. The kit of claim 46, wherein the protease is in lyophilised form.

* * * * *